US010632131B2

(12) United States Patent
Rijcken et al.

(10) Patent No.: US 10,632,131 B2
(45) Date of Patent: Apr. 28, 2020

(54) CONTROLLED RELEASE SYSTEM

(75) Inventors: Cristianne Johanna Ferdinand Rijcken, Maastricht (NL); Martin Stigter, Maastricht (NL); Josephus Johannes Maria Holthuis, Maastricht (NL)

(73) Assignee: CRISTAL DELIVERY B.V., Maastricht (NL)

(*) Notice: Subject to any disclaimer, the term of this patent is extended or adjusted under 35 U.S.C. 154(b) by 606 days.

(21) Appl. No.: 14/129,529

(22) PCT Filed: Jun. 26, 2012

(86) PCT No.: PCT/NL2012/050450
§ 371 (c)(1),
(2), (4) Date: Feb. 12, 2014

(87) PCT Pub. No.: WO2013/002636
PCT Pub. Date: Jan. 3, 2013

(65) Prior Publication Data
US 2014/0199244 A1    Jul. 17, 2014

Related U.S. Application Data

(60) Provisional application No. 61/501,288, filed on Jun. 27, 2011.

(51) Int. Cl.
| A61K 31/569 | (2006.01) |
| A61K 9/107 | (2006.01) |
| A61K 9/00 | (2006.01) |
| A61K 47/60 | (2017.01) |
| A61K 47/58 | (2017.01) |
| A61K 47/69 | (2017.01) |
| A61K 31/337 | (2006.01) |

(52) U.S. Cl.
CPC .......... *A61K 31/569* (2013.01); *A61K 9/0019* (2013.01); *A61K 9/1075* (2013.01); *A61K 31/337* (2013.01); *A61K 47/58* (2017.08); *A61K 47/60* (2017.08); *A61K 47/6907* (2017.08); *Y02A 50/465* (2018.01)

(58) Field of Classification Search
None
See application file for complete search history.

(56) References Cited

U.S. PATENT DOCUMENTS

| 5,457,172 A | 10/1995 | Curci et al. | |
| 2010/0137206 A1* | 6/2010 | Lavasanifar | A61K 9/1075 514/1.1 |

FOREIGN PATENT DOCUMENTS

| EP | 1 776 400 | 9/2005 |
| WO | WO-2007/075502 | 7/2007 |
| WO | WO-2010/033022 | 3/2010 |
| WO | WO-2011/049042 | 4/2011 |
| WO | WO-2012/039602 | 3/2012 |

OTHER PUBLICATIONS

Melhem et al (Administration of glucocorticoids to ovarian cancer patients is associated with expression of the anti-apoptotic genes SGK1 and MKP1/DUSP1 in ovarian tissues. Clin Cancer Res. May 1, 2009;15(9):3196-204).*
Robinson et al (Office-Based Intraperitoneal Chemotherapy for Ovarian Cancer. JOP Sep. 2008 vol. 4, No. 5, 225-228).*
Palliative Care Tips (http://palliative.org/NewPC/_pdfs/_tips/medadmin/ISSUE%2014_sc%20admin%20opioids_jenkins.pdf (May 2006)).*
International Search Report for PCT/NL2012/050450, dated Oct. 10, 2012, 4 pages.
Rijcken et al., "Methacrylamide-oligolactates as building blocks for targeted biodegradable polymeric micelles to deliver photosensitizers", Journal of Controlled Release (2006) 116(2):e10-e12.
Soga et al., "Thermosensitive and biodegradable polymeric micelles for paclitaxel delivery", Journal of Controlled Release (2005) 103(2):341-353.
Talelli et al., "Reprint of 'Nanobody-Shell functionalized thermosensitive core-crosslinked polymeric micelles for active drug targeting'", Journal of Controlled Release (2011) 153(1):93-102.
Banciu et al., "Antitumor activity and tumor locatlization of liposomal glucocorticoids in B16 melanoma-bearing mice," J Control Release (2008) 127:131-136.
Bontha et al., "Polymer micelles with cross-linked ionic cores for delivery of anticancer drugs," J Control Release (2006) 114(2):163-174.
Cai et al., "Intralymphatic chemotherapy using a hyaluronan-cisplatin conjugate," J Surg Res (2008) 147(2):247-252.
Dhanikula et al., "In vivo pharmacokinetic and tissue distribution studies in mice of alternative formulations for local and systemic delivery of Paclitaxel: gel, film, prodrug, liposomes and micelles," Curr Drug Deliv (2005) 2(1):35-44.
Harivardhan Reddy et al., "Influence of administration route on tumor uptake and biodistribution of etoposide loaded solid lipid nanoparticles in Dalton's lymphoma tumor bearing mice," J Control Release (2005) 105(3):185-198.
Hu et al., "Core crosslinking of biodegradable block copolymer micelles based on poly(ester carbonate)," Macromol Biosci (2009) 9(5):456-463.

(Continued)

*Primary Examiner* — Jake M Vu
(74) *Attorney, Agent, or Firm* — Morrison & Foerster LLP

(57) ABSTRACT

The present invention relates to controlled release systems that may be administered other than intravenously. The controlled release system is directed to active ingredients, entrapped in or otherwise incorporated in or coupled to polymer carriers or polymeric devices, such as micelles, nanoparticles, microspheres and other types of polymer devices for controlled release; the active ingredients are covalently bonded to the polymer carriers or polymeric devices. The controlled release systems may suitably be used to treat diseases.

21 Claims, No Drawings

(56) References Cited

OTHER PUBLICATIONS

Kim et al., "Core-stabilized polymeric micelle as potential drug carrier: increased solubilization of taxol," Polym Adv Technol (1999) 10:647-654.

Kim et al., "Polymer micelles with cross-linked polyanion core for delivery of a cationic drug doxorubicin," J Control Release (2009) 138(3):197-204.

Lee et al., "Charge-conversional polyionic complex micelles—efficient nanocarriers for protein delivery into cytoplasm," Angew Chem (2009) 121:5413-5416.

Maincent et al., "Lymphatic targeting of polymeric nanoparticles after intraperitoneal administration in rats," Pharm Res (1992) 9(12):1534-1539.

Miyata et al., "Freeze-dried formulations for in vivo gene delivery of PEGylated polyplex micelles with disulfide crosslinked cores to the liver," J Control Release (2005) 109(1-3):15-23.

Nishioka and Yoshino, "Lymphatic targeting with nanoparticulate system," Adv Drug Deliv Rev (2001) 47(1):55-64.

Nishiyama et al., "Novel cisplatin-incorporated polymeric micelles can eradicate solid tumors in mice," Cancer Research (2003) 63(24):8977-8983.

Oussoren and Storm, "Liposomes to target the lymphatics by subcutaneous administration," Adv Drug Deliv Rev (2001) 50(1-2):143-156.

Rijcken et al., "Hydrolysable core-crosslinked thermosensitive polymeric micelles: synthesis, characterisation and in vivo studies," (2007) 28(36):5581-5593.

Rijcken et al., "Novel fast degradable thermosensitive polymeric micelles based on PEG-block-poly(N-(2-hydroxyethyl)methacrylamide-oligolactates)," Biomacromolecules (2005) 6(4):2343-2351.

Sakakura et al., "Enhancement of therapeutic efficacy of aclarubicin against lymph node metastases using a new dosage form: aclarubicin adsorbed on activated carbon particles," Anti-Cancer Drugs (1992) 3:233-236.

Schiffelers et al., "Liposome-encapsulated prednisolone phosphate inhibits growth of established tumors in mice," Neoplasia (2005) 7(2):118-127.

Stenekes et al., "Polymerization kinetics of dextran-bound methacrylate in an aqueous two phase system," Polymer (2000) 41(15):5563-5569.

Bleo for Inj. 5.15.30 mg (a medical package insert), Nippon Kayaku K.K. (2009) Rev. 34, pp. 1-4.

Decision of Rejection (translation) for JP 2014-518845, dated Oct. 4, 2016, 4 pages.

Investigation of anti-tumour effect of cisplatin incorporated into PLA microcapsules (CDDP-MC), Shiga University of Medical Science (1998), thesis for doctoral degree No. 248, pp. 49-51.

The 4th Annual Meeting of the Japan Gastroenterological Association, Program and Abstracts (2008) WS-5-9, p. 197.

* cited by examiner

CONTROLLED RELEASE SYSTEM

CROSS-REFERENCE TO RELATED APPLICATIONS

This application is the national phase of PCT application PCT/NL2012/050450 having an international filing date of 26 Jun. 2012, which claims benefit of U.S. provisional patent application No. 61/501,288 filed 27 Jun. 2011. The contents of the above patent applications are incorporated by reference herein in their entirety.

The present invention relates to control release systems that may be administered via multiple routes of administration.

BACKGROUND

Controlled release system and nanoparticulate polymeric carriers such as micelles, are considered to be promising candidates for the targeted delivery of drugs. Such polymeric devices for the targeted delivery can contain a broad variety of bioactive ingredients, among which hydrophobic drugs. Reference is made to WO2010/033022 wherein a method for the preparation of a controlled control release system is disclosed. It discloses a method for entrapment of compounds in polymer carriers for controlled release of active ingredients, preferably bioactive ingredients, such as drugs. This method results in a system for controlled release of active ingredients and especially for controlled drug delivery.

In accordance with the present invention, the term "controlled release" encompasses all kinds of controlled release, including slow release, sustained and delayed release. Particularly, the present invention results in active ingredients, entrapped in or otherwise incorporated in or coupled to polymer carriers or polymeric devices, such as micelles, nanoparticles, microspheres, hydrogels and other types of polymer carriers or devices for controlled release; the active ingredients are bonded to, and especially covalently bonded to these polymeric devices or carriers.

Nanoparticulate carriers and controlled release systems are often administered intravenously, however it would be desirable to have other administration routes available. Other administration routes, such as subcutaneous administration, intralympatic administration, of liposomes and micelles have been used, but with mixed results. See for example Dhanikula et al. Curr Drug Deliv. 2005 January; 2(1):35-44, Sakakura, et al. Anti-Cancer Drugs 3 (1992), pp. 233-236, Reddy et al., J. Control Release 105 (2005) 185-198, Cai et al., J Surg Res 147, (2008) 247-252, Maincent, Pharmac Res 9 (1992) vol 12, Nishioka and Yoshino, Adv Drug Deliv Rev 47 (2001) 55-64.

Upon subcutaneous administration, nanocarriers do not have direct access to bloodstream. They either enter lymphatic capillaries draining the injection site or remain at the site of injection. Once nanoparticles traverse through interstitium to enter lymphatic capillaries, they pass through the lymphatic system where they either are captured by lymph node, or continue to reach bloodstream. For those particles remaining at the injection site, destabilization and degradation take place with time, thereby possibly releasing the therapeutic agents. This release of the therapeutic agent at the injection site, including premature or burst release as a result of an instable particle may have toxic effect and may harm the injection site, causing inflammation and discomfort to the patient. The resulting small molecules (MW<16 k Dalton) can pass through the pores in the blood capillary walls while large particles are being transported by lymphatics. The passage of small molecules, e.g. therapeutic agent, directly into the blood stream is often not desirable. The encapsulation of an agent in a nanoparticle was often intended to provide a slow or sustained release of the therapeutic agent. When the therapeutic agent is released directly into the blood stream such a sustained release is not possible anymore. When the nanoparticle is also targeted to go to a specific site, when the nanoparticle is degraded in the injection site and only the therapeutic agent is released in the blood, the targeting action is also no longer present.

According to Oussoren and Storm (Adv Drug Del Rev 50 (2001) 143-156) size is a decisive factor influencing lymphatic absorption and lymph node uptake of subcutaneous administration. Generally, other factors such as lipid composition, charge and the presence of a hydrophilic PEG-coating on the liposome surface may have an affect lymphatic absorption and lymph node uptake of s.c. administered liposomes, however the results as shown in the prior art are very mixed, and often contradict each other. It was found that about 1-2% of the injected dose is taken up by regional lymph nodes. For small (0.1 µm), neutral liposomes, the degree of lymphatic absorption can reach levels up to 70% of the injected dose. However, it should be taken into account that even after injection of liposome dispersions with a small mean size a substantial fraction of the injected dose remains at the injection site. It was also shown that the anatomical site of injection had a large influence on uptake after s.c. injection (Oussoren 2001, Adv. Drug Del Rev 50 p 143-156). After injection into the flank, liposomes remained mostly at the site of injection (about 95%), whereas injection into the foot, about 40% of the injected dose was taken up from the injection site. Also the uptake into lymph nodes was significantly lower for injection at the flank (less than 0.1%) than for injection at the dorsal side of foot or footpad (about 0.5-0.8%). It is thought that pressure in interstitial tissue is an important factor determining the uptake of liposomes from the injection site. In rats, there a less interstitial space in the foot than in the loose tissue of the flank. Injection into the foot may induce a rise in local interstitial pressure in the foot due to the limited space and thereby contribute to the increased uptake of the injected liposomes. Unfortunately the foot is not a first choice of injection site for s.c. injections.

There is thus a need for control release system such as nanoparticles and micelles that may administered other then intravenously. Preferably these particles are easily taken up by the lymphatic system and then are taken up by the lymph node and/or are passed through to the bloodstream. Preferably, the nanoparticles stay stable at the administration site and do not degrade so to release the therapeutic or active agent. It is also desirable to have a control release particle that may carry different active agents without having an effect on the uptake and/or stability of the control release particle. Preferably the control release particle may comprise linkers, such as degradable linkers, so that the covalently entrapped active agent may be released on a desired location or time. Preferably the control release particle may accommodate different linkers without an effect on the uptake and/or stability of the control release particle.

The control release systems of WO2010/033022 have all been given by intravenous administration. These particles show long circulation times in the blood circulation and because the drugs are covalently bound to the particles via biodegradable bonds they show sustained plasma levels including therapeutic levels Surprisingly it has been found that the control release system of WO2010/033022 also has good properties when administered in routes other than intravenously.

SUMMARY OF INVENTION

The present invention is directed to a method to administer a control release system to an organism wherein the administration is not intravenous. Furthermore, the present invention is directed to use of control release system to administer an active ingredient to an organism, wherein the administration is not intravenous. In addition, the present invention relates to a control release system for treatment of a disease wherein the control release system is not administered intravenously. The control release system is the system as described in WO2010/033022.

DETAILED DESCRIPTION

In WO2010/033022 a method is provided to prepare a control release system wherein active ingredients such as drug molecules are first non-covalently entrapped in polymer phases, and especially in polymer-rich phases, in an aqueous environment, and subsequently are conjugated to a 3D-polymer network.

The controlled release system of the WO2010/033022 is suitable for administration other than intravenous. An aspect of the invention is therefore related to a method to administer a control release system to an organism wherein the administration is not intravenous, wherein the control release system is obtained by
(i) mixing an active ingredient comprising a reactive moiety with an aqueous solution or dispersion comprising polymer chains comprising at least one reactive moiety, capable of reacting with the reactive moiety of the active ingredient, the polymer chains further being capable of cross-linking intra- or intermolecularly; and
(ii) subjecting this mixture to cross-linking forming a polymer matrix under such conditions that simultaneous with the formation of the polymer matrix the active ingredient is entrapped and preferably covalently entrapped in this polymer matrix.

Another aspect of the present application is therefore related to a the use of control release system to administer an active ingredient to an organism, wherein the administration is not intravenous and wherein the control release system is obtained by
(i) mixing an active ingredient comprising a reactive moiety with an aqueous solution or dispersion comprising polymer chains comprising at least one reactive moiety, capable of reacting with the reactive moiety of the active ingredient, the polymer chains further being capable of cross-linking intra- or intermolecularly; and
(ii) subjecting this mixture to cross-linking forming a polymer matrix under such conditions that simultaneous with the formation of the polymer matrix the active ingredient is entrapped and preferably covalently entrapped in this polymer matrix.

Yet another aspect of the application is therefore related to a control release system for treatment of a disease wherein the control release system is not administered intravenously and wherein the control release system is obtained by
(i) mixing an active ingredient comprising a reactive moiety with an aqueous solution or dispersion comprising polymer chains comprising at least one reactive moiety, capable of reacting with the reactive moiety of the active ingredient, the polymer chains further being capable of cross-linking intra- or intermolecularly; and
(ii) subjecting this mixture to cross-linking forming a polymer matrix under such conditions that simultaneous with the formation of the polymer matrix the active ingredient is entrapped and preferably covalently entrapped in this polymer matrix.

Yet another aspect of the present application is therefore related to treatment of a disease by administering a control release system to a organism wherein the control release system is not administered intravenously and wherein the control release system is obtained by
(i) mixing an active ingredient comprising a reactive moiety with an aqueous solution or dispersion comprising polymer chains comprising at least one reactive moiety, capable of reacting with the reactive moiety of the active ingredient, the polymer chains further being capable of cross-linking intra- or intermolecularly; and
(ii) subjecting this mixture to cross-linking forming a polymer matrix under such conditions that simultaneous with the formation of the polymer matrix the active ingredient is entrapped and preferably covalently entrapped in this polymer matrix.

In the present application, active ingredient and active molecule are used interchangeably and mean an agent with a certain activity e.g. therapeutic, preventive (e.g. vaccination), contrasting, imaging, luminescence, radiating. It is to be understood that by drug molecule an active molecule is meant, thus not only therapeutic but also including other activities.

In step (i) the polymer chains preferably interact with each other (see herein-below) forming polymer sub phases in an aqueous phase. That is, relatively, polymer chain-rich and relatively polymer chain-poor phases are created. In the best mode, the active ingredient has a preference to be present in the polymer chain rich phases. A sub-location of active ingredients in polymer chain rich sub-phases occurs based on physical interactions between the active ingredients and the polymer chains.

In step (i), the active ingredients do not form covalent conjugates with the polymer chains. Only in cross-linking step (ii) the active ingredients and the polymer chains together form a 3D-network.

The active ingredients are covalently bonded to the polymer carrier simultaneously with the cross-linking of the polymers forming the polymeric carrier or device. The cross-linked active ingredient-polymer conjugates which are formed using the method of the WO2010/033022 exhibit a higher thermodynamic stability than the non-cross-linked polymer particles. In addition, the entrapped drug molecules are prevented from rapid release due to covalent bonding to the polymeric carrier.

The method of WO2010/033022 does not require the coupling of active ingredient, such as drug molecules, directly to single polymer chains up-front, thereby fully retaining the initial properties of the polymers used, such as thermo-sensitive properties and/or the ease of drug-loaded micelle formation. The use of a fixed type of polymer, for example thermo-sensitive biodegradable block copolymers, provides a broadly applicable platform technology that allows a rapid and easy change/optimization of the composition of the active ingredient-loaded devices.

The method is applicable to all active ingredients that non-covalently interact with polymer chains that are capable of forming polymeric carriers after cross-linking. In the aqueous phase, the polymer chains (before the cross linking step) preferably assemble in a certain structure, or at least in polymer chain-rich domains; and the active ingredients localise in these assemblies. All types of physical interactions are possible (see below) but in a preferred embodiment, the active ingredients are rather hydrophobic, or at least non-hydrophilic. The only further requirement is that the active ingredient contains a moiety (or can be modified with a reactive substituent) that is capable to react with a moiety of the polymer chains that form the basis of the polymeric device or carrier.

By covalent entrapment of the active ingredient, such as drug molecules, in the core of the carrier, such as in the micellar core, the active ingredient will benefit from the prolonged circulation of the cross-linked carrier in the body and consequently lead to elevated active ingredient concentrations in desired tissue, e.g. tumour, infection, organ, or joint.

In addition, the products prepared by the method of WO2010/033022 may obtain a long term product stability by subjecting these to lyophilisation. For example, active ingredient-loaded micelles prepared according to the method of WO2010/033022 can easily be freeze-dried and subsequently resuspended without loss of morphology; as dry powder, a long shelf life is obtained.

Hence, the products as obtained by the method of WO2010/033022 comprise non covalent entrapment of active (drug) molecules in polymeric carriers in an aqueous environment, whereby the polymer chains of the polymeric carrier contain at least one reactive moiety. This non covalent entrapment is followed by a simultaneous crosslinking reaction between the optionally, yet generally, modified active (drug) molecules and the polymer chains, thereby forming an intertwined network.

The resulting active ingredient-loaded polymeric devices, such as micelles, do not display a premature release of active ingredient, but demonstrate a prolonged circulation. This results for instance in a (greatly) enhanced accumulation in the desired tissue, such as tumour, infection, organ or joint. It was also found that the control release system for use in the method of the invention and embodiments thereof have an increased stability which results in that they remain longer intact at the administration site.

When the active ingredient is entrapped via a degradable linker, a constant release of the therapeutically active compound is assured. Controlled release of the active (drug) molecules from the carrier is accomplished by cleavage of the, preferably degradable, linker or linking group between the active ingredient, such as a drug molecule, and the polymeric carrier under physiological conditions, or by local environmental triggers or external stimuli as explained and elaborated, herein-below. A suitable example of degradable linker may be found in WO2012/039602 which is incorporated by reference.

Such a linker can be exemplified by the following formula:

HOQ-$(C_nH_{2n})$—S$(R_1)(R_2)$—$(C_mH_{2m})$—$CH_2$-A, wherein n and m are integers from 0 to 20, and preferably from 1 to 10. In preferred embodiments, n is an integer from 1-5, more preferably from 1-3; and m is an integer from 1-7; more preferably from 1-5;

wherein $R_1$ and $R_2$ are independently from each other selected from an electron lone pair, an oxygen moiety, such as =O, a nitrogen moiety, such as =N—$R_x$, wherein $R_x$ is a homo- or heterogeneous group of atoms, and preferably, independently, a straight or branched $C_1$-$C_6$ alkyl, a straight or branched $C_1$-$C_6$ alkenyl, which alkyl or alkenyl group may optionally be substituted by one or more halogen groups, hydroxyl groups, amino or substituted amino groups, carboxylic acid groups, nitro groups or cyano groups; or aromatic groups, and preferably a phenyl group optionally be substituted by one or more of the substituents mentioned for the alkyl and alkenyl groups; or a halogen group, a hydroxyl group, an amino group, or a substituted amino group (the substituents being one or two $C_1$-$C_3$ alkyl groups), a carboxylic acid group, a nitro group, or a cyano group;

wherein A is a conjunction moiety; and wherein Q is a direct bond, a C=O, a C=NH or C=$NR_p$ group, wherein $R_p$ is a $C_1$-$C_3$ alkyl. In this formula the HO-Q group can be replaced by a $HR_9$N-Q group, wherein $R_9$ can either be a hydrogen atom or a $C_1$-$C_3$ alkyl group.

In the following preferred linker formula, the HO-Q group is a carboxylic acid group and the conjugation moiety A is a polymerisable methacrylate, which moieties are also exemplified in the working examples herein-below:

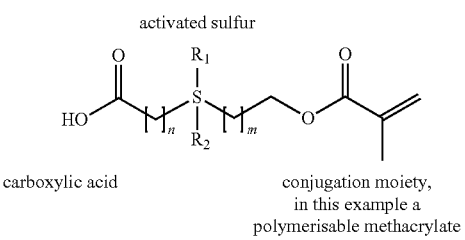

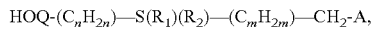

carboxylic acid          conjugation moiety, in this example a polymerisable methacrylate Suitable conjugation groups are polymerisable moieties of the formula —PL-$R_vC$=$CR_uR_w$, wherein —PL- is a linking group such as an —O—, a —NH—, a substituted —N—, the substituent being a $C_1$-$C_3$ alkyl, an —O—C(O)—, an —O—$(C(O))_r$—$C_bH_{2b}$—, wherein r is 0 or 1, and b is an integer from 1 to 6; and Ru, $R_v$ and $R_w$, independently, represent a hydrogen atom or a $C_1$-$C_3$ group.

In addition, the encapsulation prevents exposure of tissue to toxic high active ingredient peak levels that would otherwise be present immediately after administrations of free active ingredient. More importantly, by preventing migration of the drug to normal tissues, acute toxic effects may be diminished.

The other way around, the active (drug) molecules are fully protected from the environment by confinement in the formed three-dimensional network of the cross-linked polymer carrier, such as a cross-linked micellar core, thereby preventing a premature degradation and/or clearance. These unique aspects deliver the drug at the right place and time, and at an anticipated efficacious dose.

The control release system of the present invention and embodiments thereof may be derivative with a targeting ligand, i.e. to create an actively targeted nanoparticle. A targeting ligand can be anything ranging from an (radioactive) atom, a small molecule, a peptidic structure up to a full antibody or similarly large structures. The conjugation of a targeting molecule to the outside of the control release system of the present invention and embodiments thereo may be done in one step or in multiple steps optionally followed by subsequent purification to remove unconjugated ligands. This purification may be performed via e.g. dialysis or membrane centrifugation. The specific conditions of the conjugation of a targeting ligand depend on the properties of the ligand and is well within the skills of a skilled person. The targeting tissue/cells may be local in the subcutaneous area or lymph node e.g. dendritic cells or may be systemic, e.g. cancerous cells in solid tumours or in circulation. Moreover, these targeting control release system may be part of a therapeutic or a preventive therapy, such as vaccination. Targeting may be used in various indications, such as tumours, cardiovascular disease, inflammation and more.

The stepwise method of WO2010/033022 comprises two essential consecutive steps.

In the first step, a cross-linkable polymer and an active ingredient are mixed in an aqueous environment. This is preferably achieved by adding the active ingredient, optionally in a suitable solvent that preferably is water or a water miscible solvent such as a lower alcohol like ethanol, or tetrahydrofuran, to an aqueous polymer solution or dispersion. The polymer present and the active ingredient are selected so that the polymer and the active ingredient will be in intimate contact, and in a preferred embodiment, the active ingredient has a preference to be in contact with the polymer chains. Said in other words, in the first step physical, non covalent interactions between the polymer chains and the active ingredient result in the selective localisation of compounds in specific regions of a polymeric device.

As a result of the first step, the molecules forming the active ingredients are non-covalently entrapped in and between the polymer chains in solution. In the present description and the appending claims, the concept of "non-covalent interaction" means any interaction which is not covalent, i.e. any weak bonding between atoms or bonds which bonding does not involve the sharing of electron pairs. Examples of non-covalent interaction are hydrophobic, aromatic, hydrogen bonding, electrostatic, stereocomplex, and metal-ion interactions.

In the second essential step of the method of WO2010/033022, the non-covalently entrapped active ingredients are covalently coupled to the newly forming/formed polymer network. That is, a reaction is carried out, wherein the polymer chains are cross-linked. This can occur both inter- and intramolecularly, but the intermolecular cross-links are clearly preferred and any steps that favour intermolecular cross-linking are preferred embodiments of the presently claimed process. Simultaneously with the cross-linking step, the reactive moieties of the active ingredients are also co-crosslinking and an intertwined network of the polymers and the active ingredients is formed. Often, this step requires initiators, but also physical circumstances may lead to the reactions forming cross-links and conjugates. In case initiators are required, these may be added to the polymer solution together with the active ingredient, but can also added to the reaction system at an earlier or later stage.

Suitable amounts of active ingredients are amounts of 0.1-30 wt. %, preferably 0.5-15 wt. %, such as amounts of 1-10 wt. % drawn to the weight of polymer+active ingredients. Since the degree of incorporation of active ingredient may be as high as 95-100%, similar amounts may be incorporated in the formed 3D-network.

The control release particle for use in the method of the present invention and/or embodiments thereof preferably has a hydrodynamic diameter that is smaller than 100 nm, preferably 30-90 nm, more preferably, from 35 to 85 nm, more preferably from 45 to 80 nm, more preferably from 50 to 75 nm, even more preferably from 55 to 70 nm, and most preferably from 60 to 65 nm. Suitable hydrodynamic diameter are between 60 and 80 nm, more suitable between 62 and 77 nm, more suitable between 66 and 73 nm, and most suitable between 68 and 71 nm. Hydrodynamic diameters of particles may be measured by dynamic light scattering, e.g. as described in the experimental section.

Preferably, the control release particles for use in the method of the present invention and/or embodiments thereof show a narrow size distribution, i.e. preferably the sizes of the particles are homogeneous. The polydispersity index (PD) is a measure of the distribution of a molecular mass or size in a particle sample. In the context of the present invention, a PD of 1 means that the particles are completely heterogeneous of size, whereas 0 means 100% uniform. In a preferred embodiment of the present invention and/or embodiments thereof the control release particles have a PD of less than 0.25. More preferably the control release particles of the present invention have a PD of less than 0.2, more preferably less than 0.18. Suitably the control release particles of the present invention have a PD between 0.001 and 0.22, more suitably a PD between 0.01 and 0.15, even more suitably between 0.05 and 0.12 and most suitably between 0.07 and 0.1.

In a preferred embodiment the control release particle for use in a method of the invention and embodiments thereof has a surface charge that is neutral or essentially neutral. In another preferred embodiment the control release particle for use in a method of the invention and embodiments thereof has a surface charge that is negative or positive. Different coating may change the surface charge, as well as targeting ligands. A skilled person will know how to tune the surface charge of a control release particle.

According to a preferred method of WO2010/033022, amphiphilic polymers may be fully dissolved in a solvent; (bio)active compounds may be present in the solvent or may be added after the dissolution of said polymers, and the (bio)active compounds will form a general distribution over the polymer solution;

then, this system may be subjected to a change of certain circumstances (e.g. temperature, pH, solvent) leading to a situation that at least parts of the polymers display a different behaviour than other parts of the polymers and clustering takes place;

due to the physical properties of the (bio)active agents, these agents localise in certain regions of the newly formed clustered polymeric solution;

after this localisation, cross-linking takes place to fixate the (bio)active compounds in their preferred regions.

In a preferred embodiment of the method of WO2010/033022, thermosensitive block copolymers are used. For example, the active ingredient is mixed in an aqueous environment, wherein also a non-cross-linked thermosensitive block copolymer is present at a temperature lower than its Lower Critical Solution Temperature (LCST) or lower than its critical micelle formation temperature (CMT). At any temperature below this LCST, the system is in solution; at any temperature below this CMT, micelle formation does not occur. However, by heating such systems, particles or micelles are formed thereby entrapping active hydrophobic ingredients in their hydrophobic core. Next, the cross-linking reaction that forms the intertwined micellar network in the core is also carried out at a temperature higher than the LCST or the CMT. This cross-linking reaction can be accelerated by the addition of an initiator, either prior to heating of the polymer solution or after formation of the non-cross-linked particles or micelles.

Suitable polymer chains that can be used in the WO2010/033022 are, e.g., thermo-sensitive block copolymers. Particularly, copolymers based on PEG-b-poly(N-hydroxyalkyl methacrylamide-oligolactates) with partially methacrylated oligolactate units are preferred. Various other (meth)acrylamide esters can be used to construct the thermosensitive block, e.g. esters, and preferably (oligo)lactate esters, of HPMAm (hydroxypropyl methacrylamide) or HEMAm (hydroxyethylmethacrylamide), and N-(meth)acryloyl amino acid esters. Preferred thermo-sensitive block copolymers are derived from monomers containing functional groups which may be modified by methacrylate groups, such as HPMAm-lactate polymers. Other types of functional thermosensitive (co)polymers, which can be used, are hydrophobically modified poly(N-hydroxyalkyl)(meth)acrylamides, copolymer compositions of N-isopropylacrylamide (NIPAAm) with monomers containing reactive functional groups (e.g., acidic acrylamides and other moieties such as N-acryloxysuccinimide) or similar copolymers of poly(alkyl) 2-oxazalines, etc. Further preferred thermo sensitive groups can be based on NIPAAm and/or alkyl-2-oxaxolines, which monomers may be reacted with monomers containing a reactive functional group such as (meth)acrylamides or (meth)acrylates containing hydroxyl, carboxyl, amine or succinimide groups. Suitable thermo-sensitive polymers are described in U.S. Pat. No. 7,425,581 and in EP-A-1 776 400.

However, also other types of amphiphilic block copolymers or ionic micelles that are not necessarily thermo-sensitive and contain or can be modified with cross-linkable reactive groups, may be used. In such cases state-of-the-art methods can be used to form the micelles, such as direct dissolution, dialysis, and solvent-evaporation.

These other types of polymers that conform polymer-rich phases in water (e.g. due to hydrophobic interactions or ionic interactions) and that contain reactive moieties or contain moieties that can be used to couple reactive moieties, e.g. PEG-PLA-methacrylate (e.g. as described in detail in Kim et al., Polym. Adv. Technol., 10 (1999), 647-654), methacrylated PLA-PEG-PLA (e.g. as described by Lee et al. in Macromol. Biosci. 6 (2006) 846-854), methacrylated PEG-poly caprolactone (e.g. as described by Hu et al. in Macromol. Biosci. 9 (2009), 456-463), as well as other reactive moieties containing (block co)polymers based on poly lactic acid, poly lactic acid glycolic acid, and/or poly caprolactones. In addition, polymers capable of forming micelles because of ionic interactions may be used, such as block ionomer complexes of poly (ethylene oxide)-b-poly (methacrylic acid copolymers and divalent metal cations (e.g. as described by Kim et al. in J. Control. Rel. 138 (2009) 197-204, and by Bontha et al. in J. Control. Rel. 114 (2006) 163-174) polyionic complexes based on block copolymers of poly (ethylene glycol) and poly (amino acid) (e.g. as taught in Lee et al., Angew. Chem. 121 (2009) 5413-4516; in Nishi yama et al. in Cancer Res. 63 (2003), 8977-8983, or in Miyata et al., J. Control. Rel. 109 (2005) 15-23. In general, all polymers that are able to create different subphases in a suitable solvent system can be used, together with (bio)active agents that can localize selectively in such subphases.

Active ingredients to be entrapped in the polymers, include but are not limited to, drug molecules, peptides/proteins, imaging agents, genetic material or a combination of these compounds. Preferably, these active ingredients should be of a nature such that these tend to interact in a physical non-covalent manner with the polymer chains of the polymers described herein-above. In a preferred embodiment and when using the thermosensitive polymers, the method of WO2010/033022 is especially useful for encapsulation of hydrophobic compounds. Good results are obtained with active ingredients having a log P higher than 1, preferably higher than 2. For the definition of log P reference is made to Chemical Reviews 1971, volume 71, number 6. The polymer chains and the active ingredients contain or may be modified such that these contain reactive and/or polymerisable moieties, and especially free-radical polymerisable moieties, including but not limited to, terminal double bonds (e.g., vinyl groups, (meth)acrylate, (meth) acrylamide), and unsaturated compounds (e.g., linear chains containing carbon-carbon double bonds). It goes without saying that the active ingredient is selected or modified such that the free-radical initiation only leads to a bond formed from the reactive group. This guarantees that the active ingredient maintains its desired effects in the intended end-use application.

The polymers used may preferably contain a sufficiently high number of reactive substituents capable of cross-linking and reacting with the reactive groups of the active ingredients. Suitable results are obtained when for instance 10-15% of the monomer units of the polymer have a reactive substituent; however also up to 100% of the monomer units may be derivatised with reactive substituents.

The release rate of the active ingredients can easily be controlled by using different type of linkers to conjugate the reactive moiety to the active ingredients. Suitable types of well-known degradable linker molecules include but are not limited to esters, carbonates, carbamates, succinate or ortho esters, ketals, acetals, hydrazone, and enzymatically degradable linkers (e.g. peptides) or a combination of these. In addition, all kinds of well known stimuli sensitive linkers, such as photo-/temperature-/ultrasound-sensitive and other linkers can also be used. When modifying bioactive ingredients, one takes care of the type of conjugation such that upon release, only the original molecule is released and no derivatives, as to assure its therapeutic activity. By using a biodegradable linkage, the original active ingredient, such as a drug molecule, will be released according to a specific controlled release profile and subsequently exert its activity and especially its therapeutic effect.

The products obtained by the method of WO2010/033022 are polymer carriers, such as micelles, nanoparticles, microspheres, hydrogels and other types of polymer carriers or devices comprising entrapped or otherwise incorporated active ingredients for controlled release, such as devices with a coating with entrapped active ingredients. The control release system or control release particle may comprise a system or particle selected from the group consisting of micelles, liposomes, nanoparticles, microspheres, hydrogels and other types of polymer carriers or devices with a coating with entrapped active ingredients. In a preferred embodiment of the control release system or control release particle of the present invention and/or embodiments thereof the control release particle is selected from the group of micelles and nanoparticle, preferably nanoparticles.

As said, in the second essential step of the method of WO2010/033022, cross-linking and conjugation is effected. Thereto, one may use several types of (free radical) initiators for polymerisation induced cross-linking, including but not limited to, KPS (potassium persulphate)/TEMED, photo-initiators, thermo labile initiators, redox initiators, and metal ligands for ring opening metathesis polymerisation. Also living free radical polymerization techniques may be employed (for example Atom Transfer Radical Polymerisation (ATRP) and Reversible Addition Fragmentation chain Transfer (RAFT). Dependent on the end-use application of the encapsulated active ingredients, the residues of the initiators may be removed by repeated washing or by other known techniques.

By way of example, the formation of a specific embodiment of the method of WO2010/033022 is described. In this embodiment, one starts from copolymers based on PEG-b-poly(N-hydroxyalkyl methacrylamide-oligolactates) with partially methacrylated oligolactate units. Hydrophobic (drug) molecules are derivatised with a polymerisable moiety that is attached to the drug molecule via a degradable linker, such as a carbamate ester. An aqueous solution of said thermo-sensitive block copolymers is subsequently mixed with a small amount of a concentrated solution (typically 10:1 volume ratio) of (slightly) hydrophobic drug molecules in a water-miscible organic solvent (preferably with a low boiling temperature e.g. ethanol or tetrahydrofuran) at a temperature below the polymers CMT, i.e. that does not allow micelle formation. Then, an initiator solution (KPS-TEMED) is added, immediately followed by rapid heating till above the critical micelle formation temperature (CMT). This results in the formation of monodisperse polymeric micelles (size around 70 nm) where the (drug) compounds are non covalently localised in the hydrophobic core via hydrophobic interactions. After micelle formation, a nitrogen atmosphere is created. Thereby, the initiator radicals will induce polymerisation of the methacrylated polymers and the polymerisable drug compounds having a reactive moiety. This cross-linking process results in the formation of an intertwined network and fixates the drug covalently inside the micellar core, without affecting the micellar size or uniformity.

Thus, (drug) molecules are covalently entrapped in the cross-linked micelles. The micelles in this embodiment swell in a physiological environment by hydration after (partial) hydrolysis of the unmodified oligolactate units, where after the drug is released upon cleavage of the degradable linker. This cleavage can also be the result of local environmental triggers or external stimuli.

The method of WO2010/033022 is not limited to the use of polymers that can form micelles. It also allows for the non covalent entrapment and subsequent covalent cross-linking of (drug) molecules in polymeric nanoparticles, microspheres, hydrogels or coatings. With regard to the application of these devices containing (drug) compounds, WO2010/033022 encompasses the following non-limiting embodiments:
(a) controlled release of active (drug) molecules entrapped in the cross-linked micelles upon administration in vivo, e.g. by oral application, injection in the blood stream, or by direct injection in an organ or tumour;
(b) controlled release of active (drug) molecule and/or proteins entrapped in a cross-linked polymeric microspheres or a hydrogel upon localised administration; and
(c) controlled release of active (drug) molecules upon coating of a device with entrapped drug molecules, such as by dual spraying of ice cold aqueous polymer solution and drug solution (in organic solvent) onto a medical device which is kept above the phase transition temperature of the thermo-sensitive polymer. After the subsequent cross linking and the evaporation of solvents, a cross linked coating is formed.

In a preferred embodiment the control release system for use in a method of the invention and embodiments thereof has a surface density that is between 0.1 and 0.3 g/cm$^3$ preferably between 0.15 and 0.2 g/cm$^3$. In addition, the control release system for use in a method of the invention and embodiments thereof may comprise polymer chains on the surface of the control release system, e.g. PEG chains. The surface area of the control release particle shell per PEG chain (S/Nagg) is preferably 5 to 25 nm$^2$. Surface area (S) of the shell of control release system particle calculated based on hydronamic radius (Rh) is divided by the aggregation number of the control release particle (Nagg). Preferably the S/Nagg is between 7 and 20 nm$^2$, more preferably between 9 and 15 nm$^2$, and most preferably between 10 and 13 nm$^2$. The small surface area per PEG chain (i.e., higher grafting density) indicates that the control release particles have a compact structure when compared to other micellar systems, e.g., PEG-PLA copolymers.

The distance between polymer chains such as PEG chains, on the surface of a control release particles has an influence on the adsorption of plasma proteins. For instance, it has been reported that a decrease in the distance between PEG chains on the surface of polystyrene from 6.2 to 5.1 nm drastically decreases the adsorption of apolipoproteins up to 90%. The distance d can be calculated via x(4S)/∂. Preferably the control release system for use in a method of the invention and embodiments thereof has a distance between neighbouring polymer chains on the surface of the control release particle of between 2 and 10 nm, preferably between 2.5 and 8 nm, more preferably between 3 and 6 nm, more preferably between 3.2 and 4.5 nm, and most preferably between 3.5 and 4 nm. Suitably the control release particle comprises PEG chains on its surface. Preferably the distance between polymers on the surface of the control release system is small so that adsorption of serum proteins is mostly avoided. Suitably the control release particle has a distance between neighbouring polymer chains, such as PEG, of between 3 and 4 nm, more suitably between 3.2 and 3.8 nm, and more suitably between 3.4 and 3.6 nm.

The surface of the control release system of the present invention and embodiments thereof is preferably hydrophilic. The surface of the control release system of the present invention and embodiments thereof may also be hydrophobic. The surface hydrophilicity/hydrophobicity depends on the polymer chains that are present on the surface of the control release particle and may therefore be tuned to desire. Suitably the surface of the control release particle is comprised of PEG chains and will then be hydrophilic. Other suitable surface molecules are targeting ligands that may influence the hydrophylicity or hydrophobity of the control release system.

A preferred embodiment according to the present invention and/or its embodiments, the control release system is administered via a route selected from the group consisting of enteral or enteric administration, transdermal or transmucosal routes, parental administration, rectal, sublingual (under the tongue) and sublabial or buccal, (between the cheek and gums/gingiva), oral, epidural (synonym: peridural) (injection or infusion into the epidural space), intracerebral (into the cerebrum) intracerebroventricular (into the cerebral ventricles) epicutaneous (application onto the skin), topical, intradermal, (into the skin itself) subcutaneous (under the skin), nasal administration (through the nose), intraaural (in the ear), intramuscular (into a muscle), intracardiac (into the heart), pulmonal, intra-articular, intradermal, intraosseous infusion (into the bone marrow) intrathecal (into the spinal canal), intraperitoneal, (infusion or injection into the peritoneumalso intraperitonial dialysis), intravesical (infusion is into the urinary bladder), intravitreal, (through the eye), ntracavernous (into the base of the penis), intravaginal, (into the vagina), Intrauterine (into the uterus), and extra-amniotic administration, between the endometrium and fetal membranes.

Preferred administration routes are selected from the group consisting of subcutaneous, intramuscular (into a muscle), intraperitoneal (infusion or injection into the peritoneum also peritoneal dialysis), intravitreal, (through the eye), epidural (synonym: peridural), intrathecal (into the spinal canal), intracerebral (into the cerebrum, intracerebroventricular (into the cerebral ventricles), intracardiac (into the heart), intra-articular, intraosseous infusion (into the bone marrow), intracavernous (into the base of the penis), intradermal, (into the skin itself), intraaural (in the ear), intravesical (infusion is into the urinary bladder), intravaginal, (into the vagina), Intrauterine (into the uterus), extra-amniotic administration, between the endometrium and fetal membranes, rectal, pulmonal, nasal administration (through the nose), sublingual (under the tongue) and sublabial or buccal, (between the cheek and gums/gingiva), transdermal or transmucosal routes, epicutaneous, topical. More preferred administration routes according to the invention and embodiments thereof are selected from the group consisting of subcutaneous, intramuscular (into a muscle), intraperitoneal (infusion or injection into the peritoneum also peritoneal dialysis), intravitreal, (through the eye), epidural (synonym: peridural), intrathecal (into the spinal canal), intracerebral (into the cerebrum, intracerebroventricular (into the cerebral ventricles), intracardiac (into the heart), intra-articular, intraosseous infusion (into the bone marrow), intracavernous (into the base of the penis), intradermal, (into the skin itself), intraaural (in the ear), intravesical (infusion is into the urinary bladder), intravaginal, (into the vagina), intrauterine (into the uterus), extra-amniotic administration, between the endometrium and fetal membranes, rectal.

Even more preferred administration routes according to the invention and embodiments thereof are selected from the group consisting of subcutaneous, intramuscular (into a muscle), intraperitoneal (infusion or injection into the peritoneum also peritoneal dialysis), intravitreal, (through the eye), epidural (synonym: peridural), intrathecal (into the spinal canal), intracerebral (into the cerebrum, intracerebroventricular (into the cerebral ventricles), intracardiac (into the heart), intra-articular, intraosseous infusion (into the bone marrow), intracavernous (into the base of the penis), intradermal, (into the skin itself), intraaural (in the ear).

More preferred administration routes according to the invention and embodiments thereof are selected from the group consisting of subcutaneous, intramuscular (into a muscle), intraperitoneal (infusion or injection into the peritoneum also peritoneal dialysis), intravitreal, (through the eye), epidural (synonym: peridural), intrathecal (into the spinal canal), intracerebral (into the cerebrum, intracerebroventricular (into the cerebral ventricles), intracardiac (into the heart), intra-articular.

Even more preferred administration routes according to the invention and embodiments thereof are selected from the group consisting of subcutaneous, intramuscular (into a muscle), intraperitoneal (infusion or injection into the peritoneum also peritoneal dialysis), intravitreal, (through the eye), epidural (synonym: peridural), intrathecal (into the spinal canal).

Even more preferred administration routes according to the invention and embodiments thereof are selected from the group consisting of subcutaneous, intramuscular (into a muscle), intraperitoneal (infusion or injection into the peritoneum also peritoneal dialysis).

Preferred administration routes are subcutaneous, intraperitoneal, buccal, nasal, pulmonal, intra-articular, epidural, oral, topical, intradermal, intramuscular, intra-lymphatic, intravitreal. Examples of subcutaneous injection are above the knee, into the belly, into the ear, into the arm, into the hand. Preferably, sub-cutaneous injections are in areas where the skin is somewhat loose so that an injection can be easily placed under the skin. For patients it is more comfortable to inject subcutaneously in area where there is some loose skin. In addition, the injection site is preferably easily accessible especially when people are to inject themselves, for example diabetes patients or other chronic patients. It should be noted that the present invention has shown that the control release particles have an enhanced uptake from the injection site with loose skin. This is in contrast with the prior art, where only injection into the footpad, or dorsal site of the food, where the skin is tight, shows considerable uptake, whereas injection in the flank with loose skin shows that almost all of the injected dose remains at the injection site. The present invention thus enables subcutaneous injection at sites that are more comfortable for patients.

In a preferred embodiment according to the present invention and/or its embodiments the controlled release system is used for treatment of a disease. Any kind of disease may be treated with the controlled release system of the present invention. The controlled release system of the present invention is suitable for treatment of diseases including but not limited to diseases selected from the group consisting of cancer, infection, ophthalmological diseases, viral infection, bacterial infection, fungal infection, mucoplasma infection, parasite infection, inflammation, Dermatological diseases, Cardiovascular diseases, diseases of the central nerve system, auto-immune disease, proliferative diseases, arthritis, psychotic diseases, psoriasis, diabetes, metabolic disorders, lung diseases, respiratory diseases, pulmonary diseases, COPD, diseases of the muscoskeletal system, emphysema, edema, hormonal diseases. The controlled release system of the present invention is also suitable for delivery of anesthetics, and/or to be used in vaccination, being either therapeutic or preventive.

More specifically the controlled release system of the present invention and/or embodiments thereof is suitable for treatment of diseases including but not limited to diseases selected from the group consisting of spinal cord injuries, heart attacks, ischaemi, arthritis, fungal infections, post operative pain, pain, non-small cell lung cancer (or cancer-small cell lung, bladder, non-Hodgkin's lymphoma, general gastrointestinal, colorectal, head and neck, breast, general solid), acute lymphocytic and acute myelogenous leukemia, breast cancer, brain cancer, general leukaemia, liver cancer, pancreas cancer, colorectal cancer, cervical cancer, general lymphoma, ovarian cancer, squamous cell cancer, general lung cancer, pancreatic cancer, bladder cancer, renal cancer, liver cancer, small cell lung cancer, stomach cancer, Hodgkin's lymphoma, non-small cell lung cancer, oesophageal cancer, adrenal cancer, melanoma, Myelodysplastic syndrome, hairy cell leukaemia, general skin, bladder, head and neck, non-small cell lung, oesophageal, ovarian, melanoma, leiomyosarcoma, biliary, breast, prostate, systemic Lupus erythematosus, mesothelioma, and/or general sarcoma.

Moreover, the control release system of the present invention and/or embodiments thereof is suitable for treatment of disease including but not limited to a disease selected from the group consisting of diseases to the eyes, infectious diseases, inflammatory diseases, cancer, cardiovascular diseases, diseases from the central nervous system, autoimmune disease, and/or other diseases such as diabetes insipidus, polyuria, polydipsia, post-surgery pain and/or spinal cord injuries.

Infectious diseases may be selected from the group including bacterial infections including gram-negative infections, infections of skin, and/or fungal infections.

Inflammatory diseases may be selected from the group including rheumatoid arthritis, diabetes type I, diabetes type II, appendicitis, bursitis, colitis, cystitis, dermatitis, meningitis, phlebitis, rhinitis, tendonitis, tonsillitis, and/or vasculitis.

Cancer may be selected from the group including hormone sensitive prostate cancer, hormone sensitive breast cancer, non-small cell lung cancer, small cell lung cancer, bladder cancer, non-Hodgkin's lymphoma, general gastrointestinal cancer, colorectal cancer, head and neck cancer, breast cancer, acute lymphocytic leukaemia, acute myelogenous leukaemia breast cancer, brain cancer, leukaemia, liver cancer, testicular cancer, small cell lung carcinoma, ovarian cancer cervical cancer, squamous cell cancer, pancreatic cancer, renal cancer, stomach cancer, Hodgkin's lymphoma, oesophageal cancer, adrenal cancer, melanoma, Myelodysplastic syndrome, hairy cell leukaemia skin cancer, leiomyosarcoma, prostate cancer, systemic Lupus erythematosus, mesothelioma, and/or sarcoma.

Diseases to the eyes may be selected from the group including macular degeneration, acute postoperative endophthalmitis macular edema, and/or cataract.

Cardiovascular diseases may be selected from the group including vasoconstriction, coronary heart disease, ischaemic heart disease, coronary artery disease, cardiomyopathy, hypertensive heart disease, heart failure, cor pulmonale, cardiac dysrhythmias, inflammatory heart disease, endocarditis, inflammatory cardiomegaly, myocarditis, valvular heart disease, stroke and cerebrovascular disease, peripheral arterial disease, hypertension, and/or atherosclerosis.

Diseases from the central nervous system may be selected from the group including encephalitis, poliomyelitis, neurodegenerative diseases such as Alzheimer's disease, amyotrophic lateral sclerosis, autoimmune and inflammatory diseases such as multiple sclerosis or acute disseminated encephalomyelitis, and genetic disorders such as Krabbe's disease, Huntington's disease, and/or adrenoleukodystrophy.

Autoimmune diseases may be selected from the group including Acute disseminated encephalomyelitis (ADEM), Addison's disease, Agammaglobulinemia, Alopecia greata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Giant cell arteritis, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (See Autoimmune thrombocytopenic purpura), IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease (Also Amyotrophic lateral sclerosis), Lupoid hepatitis aka Autoimmune hepatitis, Lupus erythematosus, Majeed syndrome, Ménière's disease, Microscopic polyangiitis, Miller-Fisher syndrome see Guillain-Barre Syndrome, Mixed connective tissue disease, Morphea, Mucha-Habermann disease aka Pityriasis lichenoides et varioliformis acuta, Multiple sclerosis, Myasthenia gravis, Myositis, Narcolepsy[46][47], Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome another form of APS, Schnitzler syndrome, Scleritis, Scleroderma, Serum Sickness, Sjögren's syndrome, Spondyloarthropathy, Still's disease see Juvenile Rheumatoid Arthritis, Stiff person syndrome, Subacute bacterial endocarditis (SBE), Susac's syndrome, Sweet's syndrome, Sydenham chorea see PANDAS, Sympathetic ophthalmia, Systemic lupus erythematosis see Lupus erythematosis, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and/or Wegener's granulomatosis.

Other diseases may be selected from the group including diabetes insipidus, polyuria, and/or polydipsia, pruritus post-surgery pain and/or spinal cord injury including paraplegia.

Suitable embodiments for intravitreal administration include macula degeneration, acute postoperative endophthalmitis, macular edema, and/or cataract.

Suitable embodiments for subcutaneous administration include arthritis and rheumatoid arthritis, diabetes type I and diabetes type II, prostate cancer and breast cancer, including hormone sensitive prostate cancer and hormone sensitive breast cancer, cardiovascular diseases including vasoconstriction, diseases from the central nervous system including encephalitis, poliomyelitis, Alzheimer's disease, amyotrophic lateral sclerosis, multiple sclerosis, acute disseminated encephalomyelitis, Krabbe's disease, Huntington's disease, other disease such as diabetes insipidus, polyuria, and/or polydipsia.

Suitable embodiments for epidural administration include paraplegia, and/or post-surgery pain.

For the context of the present invention an organism is a multicellular organism and preferably comprises a circulatory system such as a blood system and/or preferably comprises a digestive tract and/or preferably is motile. For the present invention, animals are included in the term organism. In a preferred embodiment an organism is preferably a vertebrate, and/or a mammal, and most preferably a mammal or human.

The invention will be now illustrated by the following, non limiting example.

EXAMPLE

Example 1

Paclitaxel was modified with a methacrylate unit via a degradable ester derivative linker. The modified paclitaxel was physically entrapped by the specific embodiment based on PEG-b-poly(N-2-hydroxypropyl methacrylamide-oligolactate) with partially methacrylated oligolactate units (CMT of approx. 10° C.), and subsequently, covalently attached to the cross-linked micellar core. For details see below and WO2010/033022.

Study Set Up:

Healthy mice (approx. 8 weeks-23 gram) receive a subcutaneous or intraperitoneal (i.p.) injection and blood levels of paclitaxel (free & total) are determined after 2, 4 and 21 hours. At the latter time point, animals are sacrificed and paclitaxel concentrations (free & total) are determined. In another experiment animals receive a s.c. or i.p. injection and blood levels are determined after 3, 8 and 24 hours, as well as free and total paclitaxel determination in indicated tissues as indicated below.

| Variable | |
|---|---|
| Location | subcuteneous (s.c.) injection in upper thigh bone intraperitoneal (i.p.) injection in abdominal space |
| Drug | paclitaxel in HPMAm PM |
| Dose | 0.625 mg paclitaxel -equivalents/mouse (25 mg (paclitaxel -equivalents)/kg) Vinj ~125 µL |
| Sampling | between 2-24 hours (2-4-21 and 3-8-24) |
| Organs | Liver; Spleen; nearest lymph node; control lymph node on other side; Lung; Heart; injection site (abdomen or skin); control skin |

Example 2

Control Release Systems with Degradable Linker

Dexamethasone and paclitaxel were used as model drug compounds. These hydrophobic drug molecules were derivatised with said linkers, thereby forming biodegradable prodrugs:

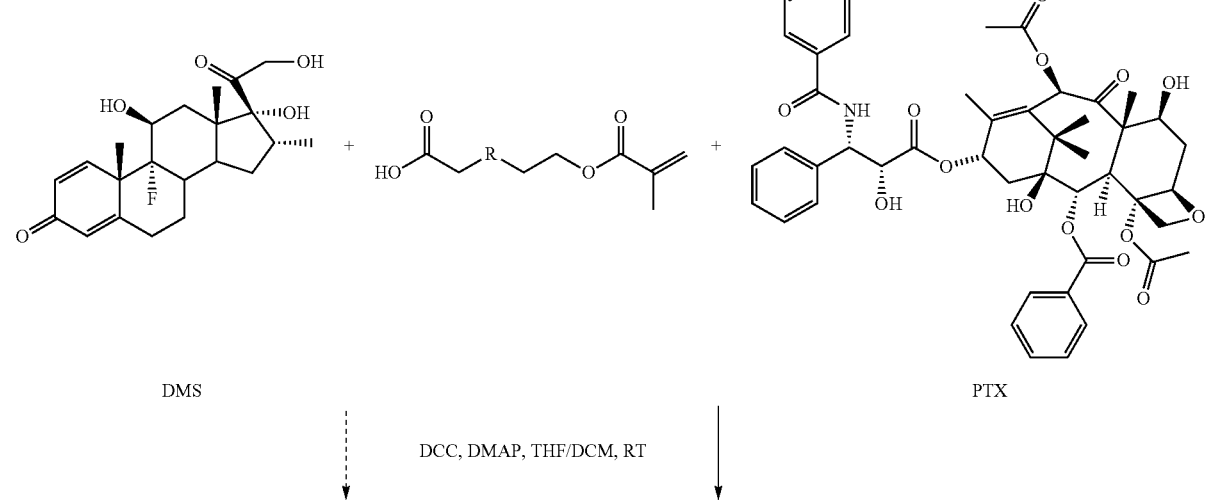

DMS

DCC, DMAP, THF/DCM, RT

PTX

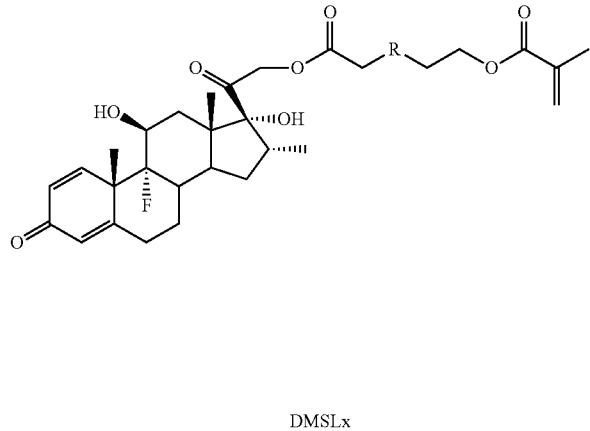

DMSLx

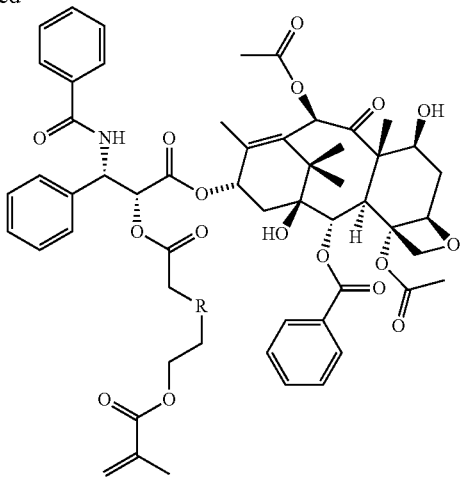

PTXLx

In this synthesis scheme, R is mono- or di-oxidized sulphur; i.e. linkers L1 (S), L2 (SO) or L3 ($SO_2$) See also WO2012/039602.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylthio)ethyl methacrylate (DMSL1)

4 (0.25 g, 1.2 mmol, 1.05 eqv.) and 4-(dimethylamino)-pyridine (DMAP) (0.077 g, 0.63 mmol, 0.5 eqv.) were dissolved in dry $CH_2Cl_2$ (20 mL) under nitrogen. The reaction mixture was cooled on ice and N,N'-dicyclohexyl-carbodiimide (DCC) (0.29 g, 1.4 mmol, 1.1 eqv.) was then added to the mixture together with DMS (0.5 g, 1.3 mmol, 1 eqv.) dissolved in dry THF (20 mL). The reaction was allowed to come to room temperature and after overnight stirring the completion of the reaction was confirmed by TLC (EtOAc/Hex, 3:2 (v/v), Hf: 0.76). Most of the solvent was evaporated and the remaining mixture was purified on a 15 cm silica gel column (EtOAc/Hex, 3:2 (v/v), Rf 0.44). 0.5 gr (70% yield) DMSL1 was obtained as a white fluffy solid.

$^1$H-NMR (DMSO): δ (ppm) 7.26 (d, 1H), 6.22 (d, 1H), 6.02 (s, 1H), 5.98 (s, 1H*), 5.68 (s, 1H*), 5.39 (s, 1H), 5.19 (s, 1H), 5.18 (d, 1H), 4.82 (d, 1H), 4.27 (t, 2H*), 3.51 (s, 2H*), 2.91 (t, 2H*), 1.87 (s, 3H*), 1.46 (s, 3H), 0.86 (s, 3H), 0.78 (d, 3H); $^{13}$C-NMR (DMSO): δ (ppm) 20.54 ($CH_3$), 21.66 ($CH_3$), 23.42 ($CH_{3*}$), 28.44 ($CH_3$), 32.73 ($CH_2$), 35.61 ($CH_{2*}$), 35.7 ($CH_2$), 37.35 ($CH_2$), 38.02 ($CH_{2*}$), 39.19 (CH), 40.87 ($CH_2$), 41.09 (CH), 48.73 (CH), 53.42 ($CH_2$), 68.55 ($CH_{2*}$), 74.11 (CH), 75.68 (C), 76.16 (C), 95.93 (CH2), 105.54 (CH), 107.85 (C), 129.52 (C), 131.43 ($CH_{2*}$), 134.41 (CH), 141.14 (C*), 158.15 (CH), 171.77 (C*), 172.46 (CH), 174.93 (C*), 190.68 (C); ESI-MS: [M+H]$^+$, calculated=579.69 d. found=578.85 d. [2M+H]$^+$. calculated=1158.38 d. found=1157.25 d.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylsulfinyl)ethyl methacrylate methacrylate (DMSL2)

5 (0.54 g, 2.4 mmol, 1.05 eqv.) was dissolved in dry THF (5 mL) and DMAP (0.14 g, 1.2 mmol, 0.5 eqv.) was added to the solution under nitrogen. After cooling on ice, a dexamethasone solution (0.91 g, 2.3 mmol, 1 eqv.) in dry THF (25 mL) and DCC (0.525 g, 2.5 mmol, 1.1 eqv.) were added to the mixture. The reaction mixture was slowly warmed to room temperature and stirred overnight at RT. The completion of the reaction was confirmed by TLC (EtOAc/Hex, 20:1 (v/v), Rf: 0.24). Most of the solvent was evaporated and the remaining solution was purified on a 20 cm silica gel column (EtOAc/Hex, 20:1 (v/v)). 1 g (73% yield) DMSL2 was obtained as a yellow fluffy solid.

$^1$H-NMR (DMSO): δ (ppm) 7.29 (d, 1H), 6.22 (d, 1H), 6.05 (s, 1H), 5.99 (s, 1H*), 5.71 (s, 1H*), 5.40 (d, 1H), 5.19 (s, OH), 5.18 (d, 1H), 4.88 (d, 1H), 4.5 (t, 2H*), 4.18 (s, 1H), 4.15 (d, 1H*), 4.00 (d, 1H*), 2.86 (s, 1H), 1.88 (s, 3H*), 1.47 (s, 3H), 0.87 (s, 3H), 0.78 (d, 3H); $^{13}$C-NMR (DMSO): δ (ppm) 20.51 ($CH_3$), 21.62 ($CH_3$), 23.32 ($CH_{3*}$), 28.34 ($CH_3$), 32.69 ($CH_2$), 35.68 ($CH_{2*}$), 35.84 ($CH_2$), 37.32 ($CH_2$), 39.80 (CH), 41.07 (CH), 48.72 (CH), 53.66 ($CH_2$), 55.53 ($CH_2$*), 61.67 ($CH_2$*), 62.72 ($CH_2$*), 74.11 (CH), 75.66 (C), 76.14 (C), 95.92 ($CH_2$), 105.54 (CH), 107.85 (C), 129.53 (C), 131.78 (CH*), 134.42 (CH), 140.94 (C*), 158.17 (CH), 170.98 (C*), 171.60 (CH*), 172.48 (C), 190.71 (C); ESI-MS: [M+H]$^+$, calculated=595.69 d. found=595.10 d. [2M+H]$^+$. calculated=1190.38 d. found=1189.65 d.

2-(2-(2-((8S,9R,10S,11S,16R,17R)-9-fluoro-11,17-dihydroxy-10,13,16-trimethyl-3-oxo-6,7,8,9,10,11,12,13,14,15,16,17-dodecahydro-3H-cyclopenta[α]phenanthren-17-yl)-2-oxoethoxy)-2-oxoethylsulfonyl)ethyl methacrylate (DMSL3)

8 (67 mg, 0.28 mmol, 1.05 eqv.) was dissolved in dry DCM (10 mL) and DMAP (0.017 g, 0.14 mmol, 0.5 eqv.) was added to the reaction mixture under nitrogen. Dexamethasone was dissolved (0.11 g, 0.27 mmol, 1 eqv.) in dry THF (10 mL). After cooling the mixture on ice DCC (0.21 g, 0.46 mmol, 1.1 eqv.) was added to the mixture together with dexamethasone. The reaction was stirred overnight at RT and the completion was confirmed by TLC (EtOAc/Hex, 7:3 (v/v), Rf: 0.47). Most of the solvent was evaporated and the remaining solution was purified on a 20 cm silica gel column (EtOAc/Hex, 7:3 (v/v)). 0.1 g (60% yield) DMSL3 was obtained as a white solid.

$^1$H-NMR (DMSO): δ (ppm) 7.29 (d, 1H), 6.22 (d, 1H), 6.05 (s, 1H), 5.99 (s, 1H*), 5.71 (s, 1H*), 5.40 (d, 1H), 5.19 (s, OH), 5.18 (d, 1H), 4.88 (d, 1H), 4.59 (s, 2H*), 4.51 (t, 2H*), 3.78 (t, 2H*), 1.87 (s, 3H*), 1.47 (s, 3H), 0.87 (s, 3H), 0.77 (d, 3H); $^{13}$C-NMR (DMSO): δ (ppm) (CH$_3$), (CH$_3$), 15.79 (CH$_3$), 16.93 (CH$_3$), 18.55 (CH$_2$), 23.63 (CH$_2$), 25.16 (CH$_2$), 27.98 (CH$_2$) 30.96 (CH), 32.59 (CH), 34.04 (CH), 36.36 (CH$_2$), 44.00 (CH$_2$), 48.75 (CH$_2$), 52.77 (CH$_2$), 58.24 (CH), 70.09 (C), 71.40 (C), 91.18 (CH$_2$), (CH), 124.80 (C), 127.25 (C), 129.69 (CH), 136.05 (CH), 153.42 (C), 163.23 (CH), 166.74 (C), 167.73 (CH), 185.96 (C), 204.66 (C); ESI-MS: [M+H]$^+$, calculated=611.69 d. found=611.05 d. [2M+H]$^+$, calculated=1222.38 d. found=1221.20 d.

The corresponding paclitaxel based compounds, PTXL1, PTXL2, PTXL3, were prepared by analogy.

Example 3

Polymer Synthesis

The used block copolymers were prepared as described by Rijcken et al., in Biomacromolecules, 2005. 6(4): p. 2343-2351 and in Biomaterials, 2007. 28(36): p. 5581-5593. The polymers contain a hydrophilic monomethoxy-PEG ($M_n$ of 5000 g/mol) block and a thermosensitive block composed of either the monolactate (36%) and dilactate (64%) of N-2-hydroxypropyl methacrylamide (HPMAm)). Subsequently, a fraction (10-15%) of the lactate side chains were methacrylated upon reaction with methacrylic anhydride as described previously in the Biomaterials reference. The molecular weight of the block copolymers and the critical micelle temperature was in all cases ~25 kDa and 8-12° C., respectively.

Example 4

Preparation of Drug-Loaded Micelles

In general terms, and in typical experiments, block copolymers were based on PEG-b-poly(N-hydroxyalkyl methacrylamide-oligolactates) with partially methacrylated oligolactate units (thermosensitive polymer). More specifically, 2 types of polymer backbones were used: 2-hydroxypropyl-methacrylamide (HPMAm). An aqueous solution of a thermosensitive block copolymer was mixed (typically 10:1 volume ratio) with a small amount of a concentrated solution of one of the prodrugs mentioned above in a water-miscible organic solvent (preferably with a low boiling temperature e.g. ethanol or tetrahydrofuran) at a temperature that does not allow micelle formation. Then, an initiator solution (KPS-TEMED, capable of producing free radicals, also other free radical initiators can be used) was added, immediately followed by rapid heating till above the critical micelle formation temperature (CMT). This resulted in the formation of monodisperse polymeric micelles where the prodrug was non covalently localised in the hydrophobic core via hydrophobic interactions. After micelle formation, a nitrogen atmosphere was created. Thereby, the initiator radicals induced polymerisation of the methacrylated polymers and the polymerisable prodrug compounds. This so-called crosslinking process resulted in the formation of an intertwined network and fixated the prodrug covalently inside the crosslinked micellar core (CCL PM).

DMS and DMS-linker-loaded micelles were prepared using the polymer based on HPMAm 14% methacrylation). An ice-cold ammonium acetate buffered (pH 5) solution of polymer (8.3 volumes, dissolved overnight at 4° C.) was mixed with KPS (0.45 volume) and TEMED (0.25 volume). DMS (prodrugs) in ethanol (1 volume) was added, followed by rapid heating to 50° C. for 1 minute while vigorously stirring. The final concentrations of polymer, KPS, TEMED and drug were 20, 1.35, 3 and 2 mg/mL, respectively. The polymers constituting each micelle were subsequently cross-linked under a N2-atmosphere for 1 hour at RT as described by Rijcken et al. in the above-cited article in Biomaterials. The KPS and TEMED concentrations were optimised to ensure complete methacrylate conversion (as described by Stenekes and Hennink in Polymer, 2000, 41(15), 5563-5569) without affecting the micellar morphology by premature polymerisation. Similarly, PTX and PTX-linker loaded micelles were prepared.

DMS-P loaded liposomes were prepared as described previously (Banciu et al. J. Contr. Release, 2008, 127(2), 131-136; Schiffelers et al., Neoplasia, 2005, 7(2), 118-127). In brief, appropriate amounts of dip almitoylphosphatidylcholine (Lipoid GmbH, Ludwigshafen, Germany), cholesterol (Sigma, St. Louis, USA), and polyethylene glycol 2000-distearoylphosphatidylethanolamine (Lipoid GmbH) in a molar ratio of 1.85:1.0:0.15, respectively, were dissolved in ethanol in a round-bottom flask. A lipid film was created by rotary evaporation. The film was hydrated with a solution of 100 mg/mL DMS-P. Liposome size was reduced by multiple extrusion steps through polycarbonate membranes (Nuclepore, Pleasanton, USA) with a final pore size of 50 nm. Mean particle size of the liposomes was determined by dynamic light scattering. Unencapsulated DMS-P was removed by dialysis in a Slide-A-Lyzer cassette with a molecular weight cut-off of 10 kDa at 4° C. with repeated changes of buffer. The aqueous phase after extraction was used for determining the glucocorticoid phosphate content by high performance liquid chromatography as described previously [8] and contained about 5 mg/mL DMS-P.

Example 5

Characterisation of Particles

Size and Size Distribution

Dynamic Light Scattering (DLS) was used to determine the hydrodynamic diameter of the particles (ZAve) and their polydisperisity (PD). The equipment consisted of a Malvern CGS-3 multiangle goniometer (Malvern Ltd., Malvern, UK) with He—Ne JDS Uniphase laser (1¼ 632.8 nm, 22 mW output power), an optical-fibrebased detector, a digital LV/LSE-5003 correlator, and a temperature controller (Julabo Waterbath). Time correlation functions were analysed using the ALV-60.0 software V.3.X provided by Malvern. Scattering of the particles solutions (at 1-2 mg/mL) was measured at an angle of 90° and at 25° C. in an optical quality 8 mL borosilicate cell. A polydispersity (PD) of 0 is a completely homogeneous mixture, a polydispersity of 1 is a completely heterogeneous mixture.

| Control release system* | $Z_{Ave}$ (nm) | PD |
|---|---|---|
| PTXL1 | 75 | 0.16 |
| PTXL3 | 73 | 0.15 |
| DMSL1 | 73 | 0.19 |
| DMSL2 | 62 | 0.05 |
| DMSL3 | 60 | 0.03 |
| Empty | 77 | 0.06 |

*all drug-entrapped control release systems were prepared with same batch of polymer.

Zetapotential measurements are based on mobility of particles induced by charge. Inherent to the principle of the measurement, neutral particles give a low signal and can therefore not be reliably assigned a ZP (hence the large Zeta deviations). All values between −10 and 10 mV can be regarded as 0. In these measurements, all ZP values were between −1 and +1 mV and thus considered neutral.

Surface charge - zeta potential

| Control release system* | Zeta potential (mV) | Zeta deviation (mV) | remarks |
|---|---|---|---|
| PTXL1 | 0 | 20 | Measured in 150 mM pH 5 |
| PTXL3 | 0 | 15 | Measured in 15 mM pH 5 |
| DMSL1 | 0 | 12 | Measured in 15 mM pH 5 |
| DMSL2 | 0 | 13 | Measured in 15 mM pH 5 |
| DMSL3 | 0 | 14 | Measured in 15 mM pH 5 |
| Empty NP | 1 | 17 | Measured in 15 mM pH 5 |

Surface Density

The surface area of the particle shell available per PEG chain (S/Nagg) was calculated for non crosslinked $PEG_{5000}$-b-p((80% $HEMAmLac_2$)−(20% $HEMAmLac_4$)) and $PEG_{5000}$-b-p($HPMAmLac_2$) micelles. Thereto, the S (surface area of the shell of micelles calculated based on hydrodynamic radius (Rh)) was divided by Nagg (aggregation number of the micelle). For the $PEG_{5000}$-b-p((80% $HEMAmLac_2$)−(20% $HEMAmLac_4$)) micelles, the Fmic and S/Nagg are 0.167 g/cm3 and 10.2 nm2, respectively. $PEG_{5000}$-b-p($HPMAmLac_2$) (Mn is 11 900) micelles gave comparable results with a Fmic of 0.16 g/cm3 and S/Nagg 12.7 nm. The small surface area per PEG chain (i.e., higher grafting density) indicates that the micelles have a compact structure when compared to other micellar systems, e.g., PEG-PLA copolymers.

The distance between PEG chains on the surface of nanoparticles (d) is critical to avoid adsorption of plasma proteins. For instance, it has been reported that a decrease in the distance between PEG chains on the surface of polystyrene from 6.2 to 5.1 nm drastically decreases the adsorption of apolipoproteins up to 90%. The distance d can be calculated via x(4S)/∂. For the $PEG_{5000}$-b-p((80% $HEMAmLac_2$)−(20% $HEMAmLac_4$)) micelles, it was calculated that the distance between neighbouring PEG chains is 3.6 nm which will likely prevent adsorption of serum proteins.

Surface Hydrophilicity

The surface of all nanoparticle is decorated with $PEG_{5000}$ chains, known to be rather hydrophilic and to prevent interactions with serum components.

Example 6

Administration of Control Release System-Subcutaneous and Intraperitoneal

PTXL1 in HPMAm NP (CriPec) was administered as 25 mg paclitaxel equivalent per kg to healthy male C57Bl/6J mice. Locations were s.c. injection at the loose tissue at the location of the upper thigh bone connecting to the flank and i.p injection in abdominal space. The s.c. injection site was chosen here as such an injection site is more comfortable for animal than injection into the foot as is done with Oussoren et al. (Adv Drug Del Rev 50 (2001) 143-156).

A group consisted of 6 mice, and blood sampling were taken between 2-24 hours (2-4-21 and 3-8-24). Animals were sacrificed after 21 and 24 hours respectively, and major tissues were taken out. Next, free and total paclitaxel levels were determined in plasma and in tissue.

Analysis of Free Paclitaxel in Plasma

One volume of plasma is diluted with one volume 0.5 M ammonium acetate buffer pH 5. Next, free paclitaxel is extracted using 4 volumes acetonitrile (final %=66% v/v).

Analysis of Total (Released Plus Entrapped) Paclitaxel in Plasma

One volume of plasma is diluted with 1 volume 0.5 M phosphate buffer pH 7.4 supplemented with 0.05% azide and incubated at 60° C. until entrapped paclitaxel is quantitatively released. Next, released paclitaxel is extracted using 4 volume acetonitrile (final %=66% v/v).

Analysis of Free Paclitaxel in Tissue

To an aliquot of tissue, 1 volume of 0.5 M ammonium acetate buffer pH 5 is added and tissue is homogenized with the Bertin homogenizer for 3×20 seconds at 5000 RPM. Homogenate is centrifuged a few seconds at 5.000 RPM. Next, free paclitaxel is extracted using 2 volumes of acetonitrile.

Analysis of Total (Released Plus Entrapped) Paclitaxel in Tissue

To an aliquot of tissue, 1 volume of 0.5 M phosphate buffer pH 7.4 supplemented with 0.05% azide is added. Tissue is homogenized with the Bertin homogenizer for 3×20 seconds at 5000 RPM. Homogenate is centrifuged a few seconds at 5.000 RPM and then incubated at 60° C. until entrapped paclitaxel is quantitatively released. Next, free paclitaxel is extracted using 2 volumes of acetonitrile.

UPLC Method:

| | |
|---|---|
| UPLC column: | HSS T3, 1.8 µm, 2.1 × 50 mm |
| UPLC VanGuard pre-column | HSS T3, 1.8 µm, 2.1 × 5 mm |
| Eluent A: | 45% ACN/55% H2O/0.1% formic acid (% v/v) |
| Eluent B: | 90% ACN/10% H2O/0.1% formic acid (% v/v) |
| Strong needle flush solvent: | 70% MeOH/20% H2O/10% IPA (% v/v) |
| Weak needle flush solvent: | 50% ACN/50% H2O (% v/v) |
| Column rinsing solution: | 50% ACN/50% H2O (% v/v) |
| Sample tray Temperature: | 5° C. |
| Column Temperature: | 30° C. |
| Flow: | 1 mL/min |
| Injection volume: | 7 µL |
| UV Detection: | 227 nm |
| Run time: | 10 minutes |

Gradient for Plasma and Tissue Extracts

| Time (min) | Flow (ml/min) | % A | % B | curve |
|---|---|---|---|---|
| 0 | 1 | 100 | 0 | |
| 4 | 1 | 100 | 0 | 6 |
| 4.5 | 1 | 0 | 100 | 6 |
| 7 | 1 | 0 | 100 | 6 |
| 7.5 | 1 | 100 | 0 | 6 |
| 10 | 1 | 100 | 0 | 0 |

Retention Time of Components

| Component | RT (min) |
|---|---|
| PTX | 1.6 |
| 7-EPI-taxol | 3.2 |

Analysis of CriPec® Dexamethasone
Analysis of Free Dexamethasone in Plasma

One volume of plasma is diluted with one volume 0.5 M ammonium acetate buffer pH 5. Next, free dexamethasone is extracted using four volumes of acetonitrile (final % v/v=66%) and samples are centrifuged for 10 minutes at 10.000 RPM. The supernatant is diluted 1:1 with water prior to analysis (final % acetonitrile=33% v/v).

Analysis of Total (Released Plus Entrapped) Dexamethasone in Plasma

One volume of plasma is mixed with two volumes acetonitrile by vortexing for 10 seconds. After centrifugation for 2 minutes at 10.000 RPM the supernatant is harvested and six volumes of 0.5 M phosphate buffer pH 12 are added. Samples are incubated at 37° C. until entrapped dexamethasone is quantitatively released and analyzed directly.

UPLC: UPLC-4

| | Type | supplier |
|---|---|---|
| UPLC column | HSS T3 | Waters |
| UPLC pre-column | HSS T3 | Waters |

UPLC Settings

| | |
|---|---|
| Eluent A | 20% ACN/80% water/0.1% formic acid (% v/v) |
| Eluent B | 90% ACN/10% water/0.1% formic acid (% v/v) |
| Strong needle wash | 70% MeOH/20% H2O/10% IPA |
| Weak wash | 20% ACN |
| Injection volume | 7 μl |
| Column Temperature | 40° C. |
| Cool tray Temperature | 37° C. |
| UV-detection | 240 nm |
| Run Time | 10 minutes |

Proposed: UPLC Gradient

| Time | Flow | % A | % B |
|---|---|---|---|
| 0 | 1 | 100 | 0 |
| 6.5 | 1 | 55 | 45 |
| 7 | 1 | 0 | 100 |
| 8 | 1 | 0 | 100 |
| 8.5 | 1 | 100 | 0 |
| 10 | 1 | 100 | 0 |

FIG. 1 shows that paclitaxel levels both as free and as total (thus free plus bound to particles) in plasma. It shows that the paclitaxel particles are absorbed by the systemic circulation mostly intact.

It was found that at least 25% of the injected dose was taken up after 28 hours. This is remarkably more uptake than as shown by Oussoren (Adv Drug Del Rev 50 (2001) 143-156). It should be noted that the injection site used in this experiment is in the loose tissue connecting the upper thigh to the flank. In Oussoren, more than 95% of the injection dose remained at the injection site, whereas in the system of the invention as shown here, less than 75% remained at the injected site. This is a huge enhancement of the uptake of the injected dose compared to the prior art.

In one mouse uptake into lymph was measured. 108 ng/mg in lymfe node was taken up, this corresponds to 16%/g tissue of the injected dose—assuming at t=0 min 100% equal distribution of the body.

FIG. 2 shows the paclitaxel level in plasma of free paclitaxel and total paclitaxel after i.p. injection. It shows that also via i.p, the paclitaxel particles are absorbed by the systemic circulation mostly intact. Furthermore, the uptake into the blood after i.p injection is almost 100%.

Comparison Between s.c. and i.v.

Setup

PTXL1 in HPMAm NP (CriPec) was administered as 25 mg paclitaxel equivalent per kg to healthy male C57Bl/6J mice. Locations were s.c. injection at the connection of the upper thigh bone to the flank. 7 groups of three mice per group were assigned to each site of injections (so total 21 mice per injection route). The seven groups were sacrificed between 1 and 14 days. From each mice, 3 blood samples were taken at an early, middle and late time points. Upon sacrifying, major tissues were taken out. Next, free and total paclitaxel levels were determined as described above.

Results

PTXL1 HPMAm NP (CriPec) were taken up in the blood stream upon s.c. injection and circulate through the blood stream for at least 96 hours. After that, the concentration was below the level of detection. FIG. 3 shows the total paclitaxel in plasma upon i.v. and s.c. administration.

The bio-availability of the subcutaneous injection is determined by dividing the Area Under the Curve of the s.c. injection by the AUC of an intravenous injection (equal dose):

AUC s.c./AUC i.v.*100=4348/12723=34% for CriPec paclitaxel(PTXL1)

S.c. Administration of Dexamethasone

Setup

The pharmacokinetic profile upon i.v. and s.c. administration of DMSL1 (CriPec) dexamethasone was determined versus free and liposomal DMS to healthy mice. Thereto, a dosage of approximately 15 mg/kg (range 13.8-20 mg/kg) was administered to healthy male C57Bl/6J mice as DMSL1, DMSL2 and DMSL3 in HPMAm NP or free dexamethasone or liposomal-dexamethasone. Blood samples were taken between 1 and 96 hours. From each mice, 3 blood samples were taken at an early, middle and late time points. At each time point, three mice were sampled. Each product was evaluated in 3 groups (so 9 mice). Upon sacrifying, major tissues were taken out. Next, free and total paclitaxel levels were determined in plasma and in tissue as described above.

FIG. 4 shows uptake of total control release particle with dexamethasone coupled to linker L1 in plasma upon i.v. and s.c. injection.

AUC total DMSL1 NP s.c./AUC total DMSL1 NP i.v.=1522/5899*100%=25.8% (dose~20 mg/kg)

FIG. 5 shows uptake of total control release particle with dexamethasone coupled to linker L2 in plasma upon i.v. and s.c. injection.

AUC total DMSL2 NP s.c./AUC total DMS2 NP i.v.=814/4344*100%=18.7% (dose~15 mg/kg).

FIG. 6 shows uptake of total control release particle with dexamethasone coupled to linker L3 in plasma upon i.v. and s.c. injection.

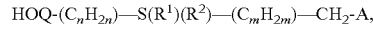

AUC total DMSL3 NP s.c./AUC total DMSL3 NP i.v.=546/2697*100%=20% (dose~15 mg/kg)

Overall, this study demonstrates that the dexamethasone control release particle are to a similar extent taken up as paclitaxel control release particles. The different type of linkers used result in reproducible uptake, between 20-25%.

It was shown that with the control release system of the present invention upon s.c. and i.p. administration that the particle remains intact:

It is taken up as integer particle and shows substantial and reproducible uptake. It was also shown that the uptake was independent on type of drug entrapped and independent of linker used. No local toxicity was found.

The invention claimed is:

1. Method to provide the bloodstream of a vertebrate subject with an intact nanoparticulate control release system comprising at least one active ingredient for systemic treatment of a disease which method comprises administering the nanoparticulate control release system via a subcutaneous or intraperitoneal route, and
   wherein the control release system is obtained by
   (i) mixing active ingredient comprising a first reactive moiety with an aqueous solution or dispersion comprising polymer chains, said polymer chains comprising at least one second reactive moiety capable of reacting with said first reactive moiety of said at least one active ingredient, the polymer chains further being capable of cross-linking intra- or intermolecularly; and
   (ii) subjecting this mixture to cross-linking forming a 3D-matrix under such conditions that simultaneously with the formation of the 3D-matrix, said at least one active ingredient is entrapped;
   wherein the polymer chains comprise polymers of hydrophobically modified esters of N-hydroxyalkyl-(meth)acrylamide and N-(meth)acryloyl amino acids; and
   wherein said at least one active ingredient is covalently coupled to the 3D matrix.

2. Method according to claim 1, wherein polymer chains include monomers derived from N-isopropylacrylamide and/or alkyl-2-oxazalines.

3. Method according to claim 1, wherein said control release system comprises micelle, hydrogel and/or coating forming polymers based on said polymers.

4. Method according to claim 1, wherein the polymer chains are di- or triblock copolymers with PEG.

5. Method according to claim 1, wherein the control release system has a hydrodynamic diameter that is smaller than 100 nm.

6. Method according to claim 1, wherein the control release system has a neutral surface charge.

7. Method according to claim 1, wherein said at least one active ingredient is a drug molecule, a peptide, a protein, an imaging agent, genetic material or a combination thereof.

8. Method according to claim 1, wherein the polymer chains and said at least one active ingredient contain polymerisable moieties.

9. Method according to claim 1, wherein the polymer chains comprise terminal double bonds or are linear chains containing carbon-carbon double bonds.

10. Method according to claim 1, wherein the active ingredient is coupled to the 3D-matrix via a degradable bond.

11. Method according to claim 1, wherein the 3D-matrix is coupled to the active ingredient via $$\text{HOQ-}(C_nH_{2n})\text{—S}(R^1)(R^2)\text{—}(C_mH_{2m})\text{—CH}_2\text{-A,}$$

wherein n and m are integers from 0 to 20;
wherein each $R^1$ and $R^2$ is independently selected from an electron lone pair, an oxygen moiety, and a nitrogen moiety;
wherein A is a conjunction moiety; and
wherein Q is a direct bond, C=O, C=NH or C=NRp, wherein Rp is a C1-C3 alkyl.

12. Method according to claim 1, wherein the control release system comprises targeted ligands.

13. Method according to claim 1, wherein the treatment is of a disease selected from the group consisting of cancer, infection, ophthalmological diseases, viral infection, bacterial infection, fungal infection, mycoplasma infection, parasite infection, inflammation, dermatological diseases, cardiovascular diseases, diseases of the central nerve system, auto-immune disease, proliferative diseases, arthritis, psychotic diseases, psoriasis, diabetes, metabolic disorders, lung diseases, respiratory diseases, pulmonary diseases, COPD, diseases of the muscoskeletal system, emphysema, edema, dementia, and hormonal diseases.

14. Method according to claim 1, wherein the at least one active ingredient is an anesthetic or therapeutic or preventive vaccine.

15. Method according to claim 1, wherein said polymer chains are (co)polymers of N-hydroxyalkyl methacrylamide-oligolactates.

16. Method according to claim 15 wherein said polymer chains are (co)polymers of (oligo)lactate esters of HPMAm (hydroxypropyl methacrylamide) or HEMAm (hydroxyethylmethacrylamide).

17. Method according to claim 5 wherein the control release system has a hydrodynamic diameter that is between 30-90 nm.

18. Method according to claim 1 wherein the polymer chain comprises vinyl groups, (meth)acrylate groups and/or (meth)acrylamide groups.

19. Method according to claim 1 wherein the vertebrate is a mammal.

20. Method according to claim 1 wherein the vertebrate is a human.

21. Method according to claim 8 wherein the polymerisable moieties are free-radical polymerisable moieties.

* * * * *